(12) United States Patent
Hessefort et al.

(10) Patent No.: US 8,158,116 B2
(45) Date of Patent: Apr. 17, 2012

(54) METHOD FOR TREATING HAIR DAMAGED BY COLOR TREATMENTS

(75) Inventors: Yin Z. Hessefort, Naperville, IL (US); Brian T. Holland, Madison, WI (US); Jeffery M. Atkins, Aurora, IL (US); Sascha Weiz, Chicago, IL (US); Xiaojin Harry Li, Bartlett, IL (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 103 days.

(21) Appl. No.: 12/346,332

(22) Filed: Dec. 30, 2008

(65) Prior Publication Data

US 2009/0220447 A1   Sep. 3, 2009

Related U.S. Application Data

(63) Continuation-in-part of application No. 12/041,081, filed on Mar. 3, 2008.

(51) Int. Cl.
*A61K 8/81* (2006.01)
*A61Q 5/06* (2006.01)

(52) U.S. Cl. ..................... 424/70.2; 424/70.16

(58) Field of Classification Search .................. None
See application file for complete search history.

(56) References Cited

U.S. PATENT DOCUMENTS

| | | | |
|---|---|---|---|
| 6,162,424 A * | 12/2000 | Decoster et al. | ........... 424/70.17 |
| 6,569,413 B1 | 5/2003 | Hessefort et al. | |
| 2006/0188455 A1 | 8/2006 | Ferenz et al. | |
| 2007/0116661 A1 | 5/2007 | Mata | |
| 2009/0220447 A1 | 9/2009 | Hessefort et al. | |

FOREIGN PATENT DOCUMENTS

| JP | 2003026544 | 1/2003 |
|---|---|---|
| WO | WO/02/085317 | 10/2002 |

OTHER PUBLICATIONS

S. B. Ruetsch, Y. K. Kamath, Aarti S. Rele, and R. B. Mohile, Secondary ion mass spectrometric investigation of penetration of coconut and mineral oils into human hair fibers:Relevance to hair damage, *Journal of Cosmetic Science*, 52, 169-184 (May/Jun. 2001).
S. B. Ruetsch and Y. K. Kamath, Penetration of cationic conditioning compounds into hair fibers: A TOF-SIMS approach, *Journal of Cosmetic Science*, 56, 323-330 (Sep./Oct. 2005).
Y. K. Kamath, S. B. Hornby, and H. D. Weigmann, Effect of chemical and humectant treatments on the mechanical and fractographic behavior of Negroid hair. *Journal of Cosmetic Science*, 36, 39-52 (Jan./Feb. 1985).
Dr. Ali Syed, "Study on the Porosity Characteristics of Damaged Hair", http://www.drailsyed.com/damage/, posted Oct. 9, 2008.
S.B. Ruetsch, Y.K. Kamath, Aarti S. Rele, and R.B. Mohile, "Secondary Ion Mass Spectrometric Investigation of Penetration of Coconut and Mineral Oils into Human Hair Fibers: Relevance to Hair Damage", J. Cosmet. Sci. 52, 169-184 (May/Jun. 2001).

\* cited by examiner

*Primary Examiner* — Tracy Vivlemore
*Assistant Examiner* — Jennifer Berrios
(74) *Attorney, Agent, or Firm* — Christopher P. Demas

(57) ABSTRACT

A method of treating one or more hair shafts, each hair shaft including a cuticle layer and a cortex enclosed in the cuticle layer is disclosed. The method comprises: selecting one or more polymers that can penetrate the hair shafts with a pore size of about 5 angstroms to about 5000 angstroms; and treating the hair shafts by applying an effective amount of a composition containing said polymers to said hair shafts.

16 Claims, 2 Drawing Sheets

METHOD FOR TREATING HAIR DAMAGED BY COLOR TREATMENTS

CROSS REFERENCE TO RELATED APPLICATIONS

This application is a continuation in part to U.S. patent application Ser. No. 12/041,081, which was filed on Mar. 3, 2008, from which filing priority is hereby claimed and the disclosure of which is hereby incorporated by reference.

BACKGROUND OF THE INVENTION

Following either popular or celebrity fashion trends, more and more consumers use hair treatments to pursue fashionable hairstyles. The color treatments include hair coloring, highlighting, and bleaching. Although these hairstyle techniques greatly satisfy consumers' needs, they also cause severe hair damage, especially when the treatments are used repetitively. Moreover, various daily actions to the hair, for example hair brushing, hair blow-drying, and sun light exposure add more damage to the hair.

It is generally accepted that chemical treatment and/or UV exposure causes hair damage, which results in increased porosity and swelling of the hair cuticle. That is why hair becomes rough, coarse and dull when damage happens to the hair. Furthermore, hair looses its tensile strength when damage occurs in the hair's cortex, since the cortex is believed to be primarily responsible for the tensile properties of human hair. The cuticle of the hair is an important factor in torsional mechanical properties, but its contribution to bulk longitudinal mechanical strength is minor. Therefore, the measurement of tensile strength not only is an evaluation method of hair damage, but also an indication to determine if damage has penetrated to the cortex. One of the ways to restore natural quality of damaged hair is to recover its reduced tensile strength.

A method of treating hair that addresses at least some of the above-mentioned problems is therefore desired.

SUMMARY OF THE INVENTION

The present disclosure provides for a method of treating one or more hair shafts, each hair shaft including a cuticle layer and a cortex enclosed in the cuticle layer of damaged hair comprising: selecting one or more PolyDADMAC polymer that can penetrate the hair shafts with a pore size of about 5 angstroms to about 5,000 angstroms; and treating the hair shafts by applying an effective amount of a composition containing said polymers to said hair shafts.

DETAILED DESCRIPTION OF THE INVENTION

Figure 1:
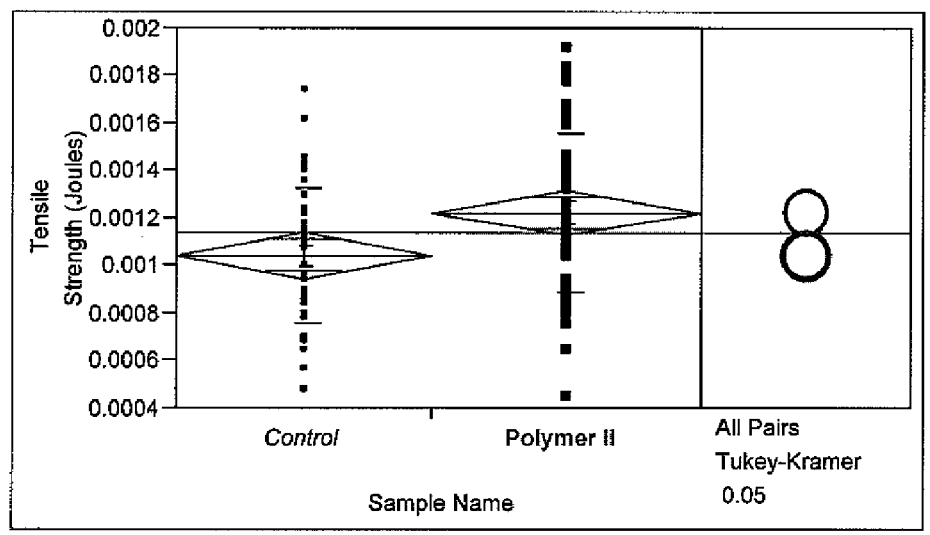
FIG. 1 shows a statistical analysis of tensile strength of Polymer II against control (no polymer addition).

Definitions: "PolyDADMAC" means poly(diallyldimethylammonium chloride).

Chemical damage hair means hair damage is caused by chemical treatment which includes hair perm, hair highlight, hair color, and hair relaxer.

Thermal damage hair means hair damage is caused by thermal treatment which includes hair blow dryer, heat hair setting.

UV damage hair means hair damage is caused by excess UV exposure.

As stated above, one or more hair shafts are treated with one or more polymers that can penetrate a hair shaft with a pore size of about 5 angstroms to about 5000 angstroms.

In one embodiment, the hair shaft pore size is between about 10 angstroms and about 1000 angstroms.

In another embodiment, the purpose of the treatment is to nourish and/or repair the hair shaft.

In another embodiment, the purpose of the treatment is to improve the tensile strength of the hair.

Generally, the polymers utilized should be of sufficient size to penetrate into the cortex of the hair shaft, but not easily migrate out of the cortex. One of ordinary skill in the art could determine whether a polymer meets this particularly criteria without undue experimentation. Therefore, polymers that are linear, branched, hyperbranched, or dendritic may meet this criteria.

Various types and conformations of polymers may be utilized to treat a hair shaft.

In one embodiment, the PolyDADMAC polymer is selected from the groups consisting of homopolymers, copolymers, terpolymers, and a combination thereof.

In another embodiment, the PolyDADMAC polymer is selected from the group consisting of cationic polymers.

In another embodiment, the PolyDADMAC polymer is selected from the group consisting of: PolyDADMAC, poly(sodium acrylate), and a combination thereof.

In another embodiment, the polymers have a weight average molecular weight of from about 300 daltons to about 80,000 daltons, excluding PolyDADMAC wherein the upper limit of said range for PolyDADMAC is less than 15,000 daltons.

In another embodiment, the PolyDADMAC has a weight average molecular weight of from about 1,500 to less than 15,000.

In another embodiment the range for the weight percent of the PolyDADMAC is 0.1% to about 10% weight percent, based upon actives in said composition.

In another embodiment, the PolyDADMAC has the weight average molecular weight of about 1,200 daltons to about 5,700 daltons.

In another embodiment, the poly(sodium acrylate) has a weight average molecular weight of about 300 daltons to about 30,000 daltons.

In another embodiment, the poly(sodium acrylate) has a weight average molecular weight of about 3,000 daltons to about 15,000 daltons.

Hair shafts are damaged in various ways, e.g. by overprocessing hair, more specifically, colored hair, relaxed hair, over-bleaching hair, UV-exposure to hair, thermal treatment of hair and/or by environmental stress.

In one embodiment, the polymers are utilized to treat hair that is chemically damaged and/or UV damaged and/or thermal damaged.

In another embodiment, the polymers may be utilized to prevent hair from being damaged or inhibit the rate at which hair is damaged, or repair the damaged hair.

The composition may further comprise one or more cosmetically acceptable excipients. A cosmetically acceptable excipient is a non-toxic, non-irritating substance which when mixed with the one or more polymers of this invention makes the polymers more suitable to be applied to the hair.

In one embodiment, the excipients are selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, mono, di or tri-long chain amines from about $C_{10}$ to $C_{22}$, long chain fatty amines from about $C_{10}$ to $C_{22}$, fatty alcohols, ethoxylated fatty alcohols and di-tail phospholipids.

The composition containing the PolyDADMAC polymer may be in various forms. One of ordinary skill in the art would know how to formulate the polymers with cosmetically acceptable excipients and/or other components of a composition.

In one embodiment, the composition is selected from the group consisting of shampoos, conditioners, permanent waves, hair relaxers, hair bleaches, hair detangling lotion, styling gel, styling glazes, spray foams, styling creams, styling waxes, styling lotions, mousses, spray gets, pomades, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

The following example is not meant to be limiting.

EXAMPLE

For this EXAMPLE section, the weight-average molecular weight of polymer was determined by a size-exclusion chromatography/multi-angle laser light scattering (or SEC/MALLS) technique. Size exclusion chromatography (SEC) was performed by using a series of TSK-GEL PW columns from TOSOH BIOSCIENCE, a multi-angle laser light scattering detector (MALLS, model: DAWN DSP-F) and an interferometric refractometer (OPTILAP DSP) from Wyatt Technology. Data collection and analysis were performed with ASTRA software from Wyatt Technology.

| Key for Example | | |
|---|---|---|
| Polymer | Chemistry | Molecular Weight |
| I | PolyDADMAC | 1,300 |
| II | PolyDADMAC | 3,800 |
| III | PolyDADMAC | 5,700 |
| IV | PolyDADMAC | 150,000 |

Example Particulars a. Tensile Strength Measurements

A tensile strength test was done on chemically damaged hair. The protocol included the following steps.

Virgin brown hair was bleached by immersion in 6% hydrogen peroxide solution containing 1.7% ammonium hydroxide and 10% urea at 40±1° C. for 15 minutes. The bleached hair was then treated in 1% (solid) polymer solution for 5 minutes and rinsed under deionized water for 10 seconds.

The diameter of forty hair strands was randomly selected from each treated and untreated ("control") testing group were measured using a Fiber Dimensional Analysis System (Mitutoyo, Model LSM 5000). The hair samples were placed in a DiaStron Miniature Tensile Tester (Model 170/670) for the determination of tensile strength in a wet condition. The total work force normalized with hair diameter was calculated by using DiaStron software (MTTWIN Application Software Version 5.0). The mean values obtained from 40 hair strands were analyzed using Tukey HSD statistical analysis to compare all the testing pairs (ANOVA one-way analysis of variance from JMP statistical software, SAS Institute, Cary, N.C., U.S). The testing results and statistical analysis are summarized in following tables and figures. Results for cationic polymers are shown in Table 1 and Table 2. Results for anionic polymers are shown in Table 3 and Table 4.

TABLE 1

| Chemistry and Molecular Weight of the Cationic Polymers | | |
|---|---|---|
| Name | Molecular Weight | Chemistry |
| Polymer IV | 150,000 | PolyDADMAC |
| Polymer II | 3800 | PolyDADMAC |

TABLE 2

| Tensile Strength Measurement for the Treatment Listed in Table 1 | | |
|---|---|---|
| Sample Name | Tensile Strength (J) | % Improvement |
| Control | 0.00104 | |
| Polymer IV | 0.00107 | ≈0 |
| Polymer II | 0.00122 | 17.31 |

Figure 2:
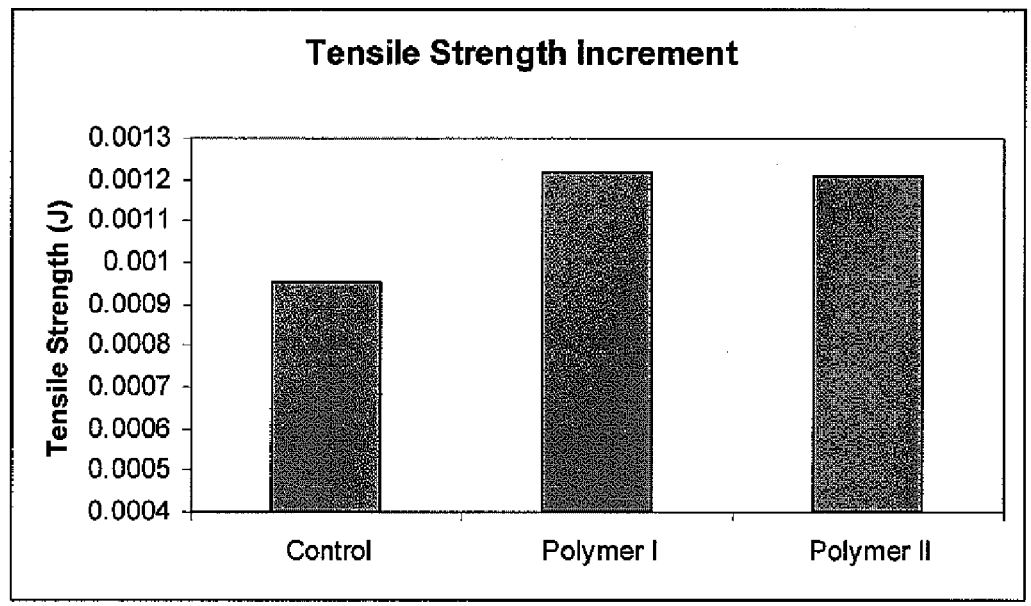
FIG. 2 shows a tensile strength increment of Polymer I and II against control (no polymer addition).
Figure 3:
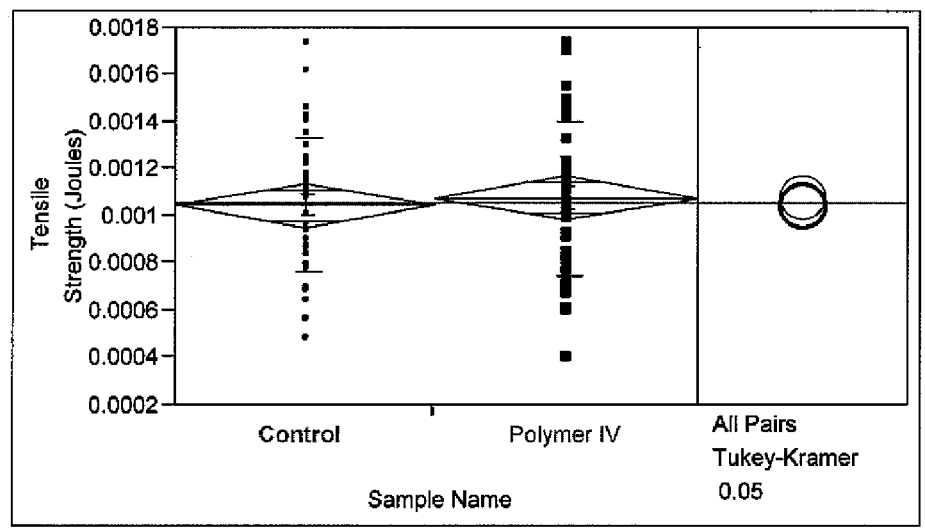
FIG. 3 shows a statistical analysis of tensile strength of Polymer IV against control (no polymer addition).
Figure 4:
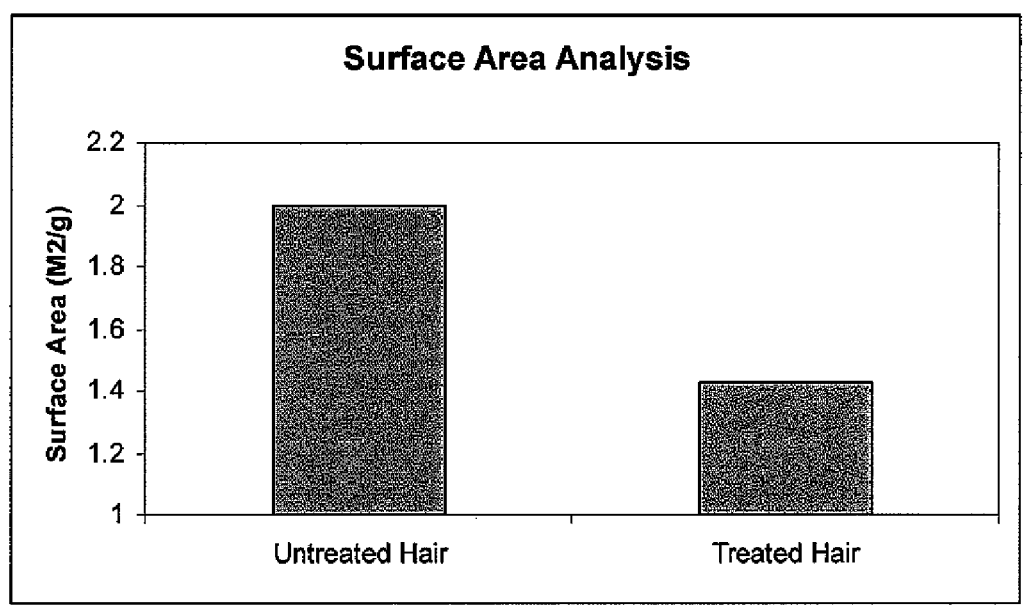
FIG. 4 shows a surface area analysis study of hair treated with Polymer II and control (no polymer addition).

It is clear from Table 1, Table 2, and FIG. 1 that the low molecular weight of Polymer II significantly improves tensile strength for about 17% while statistical analysis shows that there is no significant difference in tensile strength between control and Polymer IV (FIG. 3). Experiments were performed with Polymer I, a low molecular weight PolyDADMAC. The results are shown in FIG. 2. These results show that the penetration of the low molecular weight polymer can recover the lost tensile strength of damaged hair.

b. Surface Area Measurements

Surface area analysis was also done both on treated and untreated hair tresses to understand if low molecular weight polymer species penetrated the hair shaft. The protocol included the following steps.

Surface area analysis was carried out via a nitrogen adsorption analysis. Nitrogen adsorption analyses on hair samples were conducted using a Quantachrome Autosorb-1C instrument. Samples were cut to very fine pieces and then added to a sample cell where they were placed under vacuum at 145° C. for 0.5 hours. Complete water removal is necessary to obtain accurate measurements, which is why 145° C. was used. This value is based on the data collected from Differential Scanning Calorimetry (DSC) in which dehydration peak appears at around 125° C. A 5-pt BET (Brunauer-Emmett-Teller) surface area analysis was used for all samples. The decrease of surface area indicates that the low molecular weight polymers penetrated the hair and took up the pore spaces, which are distributed throughout the hair shaft.

The results for the surface analysis study are illustrated in FIG. 5. Gas sorption analysis from FIG. 5 shows the significant decrease in surface area of hair shafts treated with Polymer II, which illustrates the effective penetration of low molecular weight polymers into the hair shafts.

We claim:

1. A method of treating one or more hair shafts, each hair shaft including a cuticle layer and a cortex enclosed in the cuticle layer of chemical, UV, thermal and environmental damaged hair comprising: selecting one or more PolyDADMAC polymers having a weight average molecular weight of less than 5,000 Daltons that can penetrate the hair shafts with a pore size of about 5 angstroms to about 5000 angstroms; and treating the hair shafts by applying an effective amount of a composition containing said PolyDADMAC polymer to said hair shafts.

2. The method of claim 1 wherein said chemical damage includes bleaching, highlighting, relaxing or coloring of the hair.

3. The method of claim 1 wherein said polymers are selected from the groups consisting of homopolymers, copolymers, and terpolymers, and a combination thereof.

4. The method of claim 1 wherein said polymers are selected from the group consisting of cationic polymers.

5. The method of claim 1 wherein said polymers are linear.

6. The method of claim 1, wherein the composition further comprises polysodium acrylate.

7. The method of claim 6 wherein the weight percent of said PolyDADMAC is from about 0.1% to about 10%, based upon actives in the composition.

8. The method of claim 6 wherein said poly(sodium acrylate) has a weight average molecular weight of about 300 daltons to about 30,000 daltons.

9. The method of claim 6 wherein said poly(sodium acrylate) has a weight average molecular weight of about 3,000 daltons to about 15,000 daltons.

10. The method of claim 6 wherein said poly(sodium acrylate) has a weight average molecular weight of about 300 daltons to about 6,000 daltons.

11. The method of claim 1 wherein said composition contains one or more cosmetically acceptable excipients.

12. The method of claim 1 wherein said excipients are selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

13. The method of claim 1 wherein said composition is selected from the group consisting of shampoos, conditioners, permanent waves, hair bleaches, hair detangling lotion, styling gel, styling glazes, spray foams, styling creams, styling waxes, styling lotions, mousses, spray gels, pomades, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

14. The method of claim 1 wherein said pore size is from about 10 angstroms to about 1,000 angstroms.

15. The method of claim 1 wherein said PolyDADMAC polymers have a weight average molecular weight of 3,800 Daltons.

16. The method of claim 1 wherein said PolyDADMAC polymers have a weight average molecular weight of 1,300 Daltons.

* * * * *